(12) United States Patent
LeMay et al.

(10) Patent No.: US 10,695,230 B2
(45) Date of Patent: *Jun. 30, 2020

(54) ERGONOMIC TAMPON APPLICATOR

(71) Applicant: Edgewell Personal Care Brands, LLC, Chesterfield, MO (US)

(72) Inventors: Jessica LeMay, Portland, OR (US); Kathryn Bennett, Fairfield, CT (US); Keith Edgett, Middletown, DE (US); Dane Jackson, Bloomingdale, NJ (US); Mario Turchi, Tenafly, NJ (US); Susanne Weber, New York, NY (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,586

(22) Filed: Apr. 13, 2017

(65) Prior Publication Data

US 2017/0216103 A1 Aug. 3, 2017

Related U.S. Application Data

(63) Continuation of application No. 15/188,032, filed on Jun. 21, 2016, now Pat. No. 9,662,249, which is a continuation of application No. 14/576,473, filed on Dec. 19, 2014, now Pat. No. 9,737,443, which is a continuation of application No. 13/669,840, filed on Nov. 6, 2012, now Pat. No. 9,421,135, which is a continuation of application No. 12/798,990, filed on Apr. 15, 2010, now Pat. No. 8,337,478, which is a continuation of application No. 10/242,474, filed on Sep. 12, 2002, now Pat. No. 7,727,208.

(51) Int. Cl.
*A61F 13/15* (2006.01)
*A61F 13/26* (2006.01)
*A61F 13/20* (2006.01)
*A61F 13/34* (2006.01)

(52) U.S. Cl.
CPC ............ *A61F 13/266* (2013.01); *A61F 13/26* (2013.01); *A61F 13/2077* (2013.01); *A61F 13/263* (2013.01); *A61F 13/34* (2013.01); *Y10S 604/904* (2013.01)

(58) Field of Classification Search
CPC .... A61F 13/266; A61F 13/26; A61F 13/2077; A61F 13/263; A61F 13/34; Y10S 604/904
USPC .............. 604/385.17, 385.18, 904, 285, 286, 604/11–18, 311
See application file for complete search history.

(56) References Cited

U.S. PATENT DOCUMENTS

D250,663 S * 12/1978 Koch .............................. 604/14
5,437,628 A * 8/1995 Fox .......................... A61F 13/26
604/1

\* cited by examiner

*Primary Examiner* — Jacqueline F Stephens

(57) ABSTRACT

A tampon applicator barrel includes an insertion tip at a forward end of the barrel, a main body section that extends from the insertion tip, and a reverse taper section that is joined to the main body section so that the main body section is between the insertion tip and the reverse taper section. The main body section tapers toward the insertion tip section. The reverse taper section tapers in a direction away from the insertion tip section. A finger grip section extends from the reverse taper section to a plunger receiving end of the barrel opposite the forward end. The barrel is straight from the forward end to the plunger receiving end that receives a plunger.

18 Claims, 2 Drawing Sheets

ERGONOMIC TAMPON APPLICATOR

CROSS-REFERENCE TO RELATED APPLICATIONS

This is a continuation application of pending U.S. application Ser. No. 15/188,032, filed Jun. 21, 2016, which is a continuation application of pending U.S. patent application Ser. No. 14/576,473, filed on Dec. 19, 2014, which is a continuation application of U.S. patent application Ser. No. 13/669,840 filed Nov. 6, 2012, which is a continuation application of U.S. patent application Ser. No. 12/798,990, filed Apr. 15, 2010, which is a continuation application of U.S. patent application Ser. No. 10/242,474, filed Sep. 12, 2002. Each of the above-noted applications is incorporated herein by reference.

BACKGROUND OF THE INVENTION

A. Field of Endeavor

The disclosure relates generally to an improved tampon or tampon applicator. More particularly, the present disclosure relates to a tampon applicator with a barrel that has a reverse taper section for improved ease of use and user comfort.

B. Description of the Prior Art

Commercial tampon applicators typically consist of a barrel and a plunger used to expel an absorbent pledget housed in the barrel. The barrel is typically sub-divided into three sections, namely a finger grip, an insertion tip, and a main body section, which is located between the finger grip and insertion tip sections.

The finger grip section is typically the same diameter as the main body section of the barrel, but some designs (e.g., Playtex® Gentle Glide®) have a reduced diameter grip for improve grippability. The main body section is typically linear, except on plastic molded barrels where there is a slight taper to improve release characteristics from the manufacturing mold. The insertion tip section on some types of barrels have "petals" which curve over and enclose the pledget (i.e., rounded tip) housed in the barrel, but readily flex outwardly as the pledget is expelled through the insertion tip.

SUMMARY OF THE INVENTION

The present disclosure provides a tampon applicator that is ergonomic.

The present disclosure also provides such an ergonomic tampon applicator with a plunger and a barrel.

The present disclosure further provides such an ergonomic tampon applicator barrel having a finger grip section, a reverse taper section, a main body section and an insertion tip section.

The present disclosure still further provides such an ergonomic tampon applicator barrel reverse taper section where the reverse taper is towards the finger grip section.

The present disclosure also provides such an ergonomic tampon applicator barrel finger grip section having a finger accepting region.

The present disclosure further provides such an ergonomic tampon applicator insertion tip section formed with a plurality of petals.

The present disclosure still further provides such an ergonomic tampon applicator main body section with a maximum diameter section that is sensually perceivable to a user to alert the user to the proper insertion depth of the applicator.

The present disclosure also provides such an ergonomic tampon applicator having a plunger with at least one flared end.

These and other objects and advantages of the present disclosure will be appreciated from an ergonomically improved tampon applicator having a plunger and a barrel, of the present disclosure. The barrel has four distinct sections, namely a finger grip section, a reverse taper section, a main body section, and an insertion tip section. The reverse taper section is tapered towards the fingergrip section, and the main body section is tapered in an opposite direction towards the insertion tip section. A maximum diameter is formed where the reverse taper section and main body section meet on the barrel. The maximum diameter provides a sensory indicator to the user to alert the user when the applicator has been inserted to the proper depth in the vagina.

DETAILED DESCRIPTION OF THE INVENTION

Figure 1:
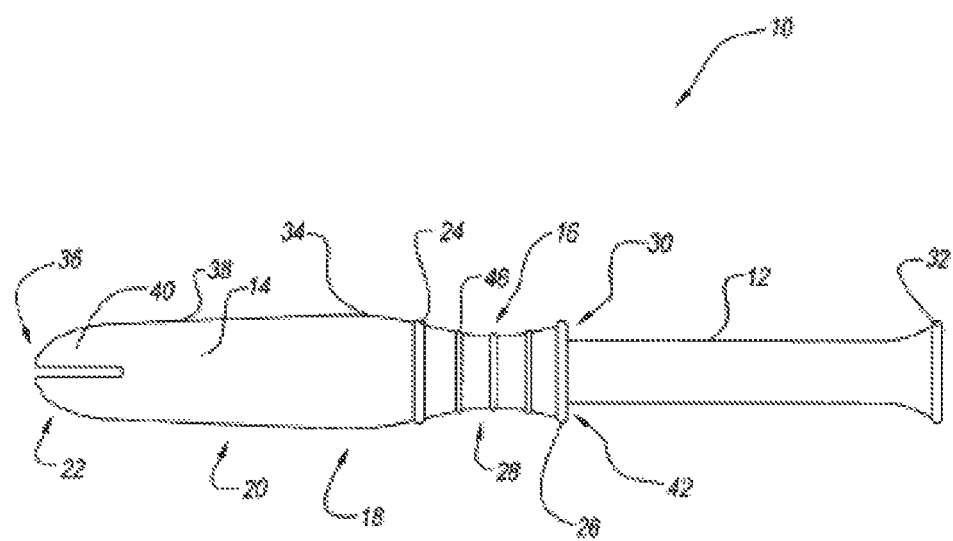
FIG. 1 is a plan view of a tampon applicator of the present disclosure.

Referring to FIG. 1, drawings and, in particular, FIG. 1, there is shown an ergonomically improved tampon applicator according to the present disclosure generally represented by reference numeral 10. The ergonomically improved applicator 10 is easier to use and more comfortable to insert and remove. Applicator 10 includes a plunger 12 and a barrel 14.

Barrel 14 may be divided into four sections, as opposed to three sections typically found in prior art tampon applicators. The four sections include a finger grip section 16, a reverse taper section 18, a main body section 20, and an insertion tip section 22.

Finger grip section 16 is bound by a forward edge ridge 24 and a rearward edge ridge 26. Forward edge ridge 24 provides a firm grip surface during insertion of applicator 10 into the vaginal vault, Rearward edge ridge 26 provides a firm grip surface during expulsion of the pledget (not shown) and during removal of applicator 10 from the body. Forward and rearward edge ridges 24, 26 are about 6 mm to about 22 mm in diameter. Preferably, the forward and rearward edges 24, 26 are about 11 mm to about 17 mm in diameter, with about 14 mm being the most preferred diameter.

A finger accepting region 28 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart. More preferably, forward edge ridge 24 and rearward edge ridge 26 are spaced about 17 mm to about 21 mm apart, with about 19 mm being the most preferred spacing. Finger accepting region 28 may be concave, convex, flat, or any combinations thereof. Preferably, region 28 is concave, which conforms to the contour of a user's finger. The maximum diameter of region 28 is preferably slightly less than the diameter of edge ridges 24, 26. Preferably, region 28 has a maximum to minimum diameter ratio of about 1.10 to about 1.75, with a more preferred ratio of about 1.25 to about 1.35.

Finger accepting region 28 may also include one or more gripping structures 46 to improve grippability of applicator 10. Suitable gripping structures 46 include, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 14 occurs at the forward end of reverse taper section 18. Reverse taper is meant to include a taper in the reverse direction, i.e. in a direction away from the insertion end of applicator 10, but not necessarily the same dimensional taper as main body section 20, The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 14 exerts a slightly greater pressure than the smaller diameter portions of the barrel on the vaginal opening. This unique feature of barrel 14 provides a sensually perceivable way of signaling or indicating to a user that applicator 10 has been inserted to the correct depth in the vagina. Thus, the location of maximum diameter 34 along the length of barrel 14 is a critical aspect of the present disclosure. The location of maximum diameter 34 on barrel 14 is about 32 mm to about 54 mm in the axial direction of barrel 14 from forward end 36 of insertion tip 22. Preferably maximum diameter 34 is located about 40 mm to about 50 mm, and more preferably about 44 mm in the axial direction of barrel 14 from forward end 36 of insertion tip 22.

Main body section 20 is joined to reverse taper section 18 where maximum diameter 34 of barrel 14 is located. Main body section 20 tapers toward insertion tip section 22 in either a linear or curvilinear fashion so that its smallest diameter occurs where main body section 20 meets insertion tip section 22. The ratio of maximum diameter 34 to the diameter at the forward end 38 of main body section 20 is about 1.1 to about 1.5, and more preferably about 1.2 to about 1.3. This tapering of main body section 20 facilitates insertion comfort by gradually parting the vulva-vaginal channel over a longer length than that of only insertion tip section 22.

Insertion tip section 22 begins where there is a substantial change in the curvature of the forward portion of the barrel that is where the pledget-enclosing petals 40 are formed. In applicator designs where no petals are used, insertion tip 22 is the forward edge of the main body section 20 of barrel 14. The preferred insertion tip 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a horizontal axis of applicator 10, is about 0.9 to about 1.8, and more preferably about 1.1 to about 1.3.

The less severe curvature of insertion tip section 22 also facilitates insertion comfort by gradually parting the vulva-vaginal channel along its longer length.

It should be understood that while tampon applicator barrel 14 of the present disclosure is depicted as having four sections, namely a finger grip section, a reverse taper section, a main body section, and an insertion tip section, the tampon applicator barrel can include a reverse taper section and at least one additional section selected from a finger grip section, a main body section, an insertion tip section, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Figure 2:
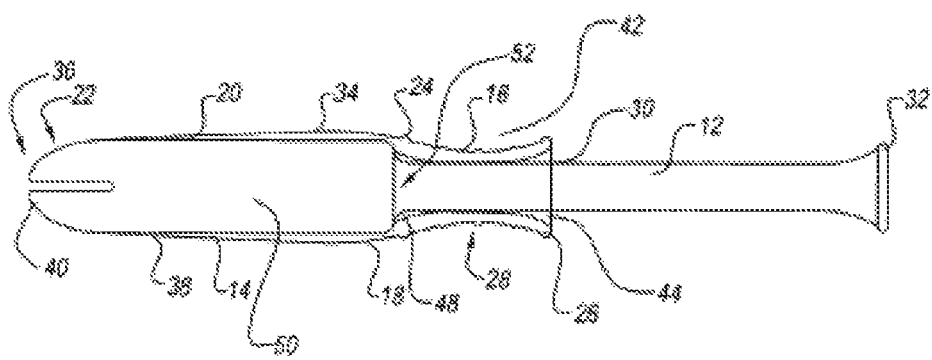
FIG. 2 is a cut away view of the tampon applicator of FIG. 1 depicting an absorbent pledget housed in the barrel.
Figure 3:
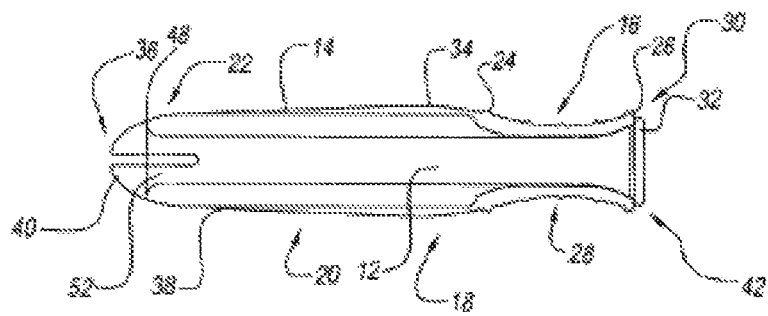
FIG. 3 is a cut away view of the tampon applicator of FIG. 2 after the pledget has been expelled from the barrel.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of finger receiving region 28 so that plunger 12 telescopically fits throughout the interior of barrel 14. Preferably, in one embodiment of the present disclosure, plunger 12 has a diameter about 4 mm to about 18 mm. More preferably, plunger 12 has a diameter about 5 mm to about 9 mm with the most preferred diameter being about 7 mm.

Plunger 12 has a first flare 32 at its distal end and a second flare or retaining structure 48 at its opposite barrel end 52. Finger grip section 16 has a plunger receiving end 30. Plunger receiving end 30 of finger grip section 16 has a chamfer 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator, Such an ergonomic applicator is conducive to one handed use, since the distance between finger grip section 16 and first flare 32, where the fingertip is placed, is reduced by an amount equal to the length of first flare 32. Second flare or retaining feature 48 on barrel end 52 of plunger 12 prevents separation from barrel 14.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The pledget housed by applicator barrel 14 preferably has a tapered forward end that corresponds to that of insertion tip 22. The matching taper supports petals 40 during insertion of applicator 10 so that the petals cannot flex out of shape, thus enhancing comfort. Additionally, during expulsion from applicator 10, the pledget's tapered tip will gradually part the vaginal channel, further enhancing user comfort.

Suitable materials for forming plunger 12 and/or barrel 14 include, for example, biopolymer, cardboard, heat shrink plastic, paper slurry, plastic, plastic tubing, pulp slurry, pulp-molded paper, or any combinations thereof.

To reduce friction and/or increase strength, plunger 12 and/or barrel 14 may be coated with a coating material. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

The foregoing specification and drawings are merely illustrative of the present invention and are not intended to limit the invention to the disclosed embodiments. Variations and changes, which are obvious to one skilled in the art, are intended to be within the scope and nature of the present invention, which is defined in the appended claims.

The invention claimed is:

1. A plastic tampon applicator, comprising:
an insertion tip section having between three and eight petals;
a main body section having a first end adjacent said insertion tip section, said main body section having a main body maximum diameter of said tampon applicator;
a reverse taper section adjacent said main body section, said reverse taper section having a reverse taper maximum diameter that is less than said main body maximum diameter;
a finger grip section having a forward end adjacent said reverse taper section, the finger grip section having a flared rearward end opposite said forward end defining an opening, wherein said finger grip section has at least one gripping structure, the finger grip section having a circular cross-sectional shape,
wherein said finger grip section has a finger grip minimum diameter that is less than said main body maximum diameter of said main body section,
wherein said at least one gripping structure has a grip structure diameter that is less than a flared rearward end diameter of said flared rearward end,
wherein said ratio of said finger grip maximum diameter to said finger grip minimum diameter is between about 1.25 and about 1.35,
wherein said tampon applicator has a straight central axis, said insertion tip section, said main body section, said reverse taper section, and said finger grip section are all coaxially positioned around said central axis of said tampon applicator,
wherein said petals have a curved shape such that a tip of each petal tapers towards said central axis.

2. The tampon applicator according to claim 1, wherein said finger grip minimum diameter is less than said reverse taper maximum diameter.

3. The tampon applicator according to claim 1, wherein said grip structure diameter is less than said reverse taper maximum diameter.

4. The tampon applicator according to claim 1, wherein said finger grip section has a forward edge ridge adjacent said reverse taper section.

5. The tampon applicator according to claim 4, wherein said forward edge ridge has a forward edge ridge diameter greater than a minimum reverse taper diameter.

6. The tampon applicator according to claim 4, wherein said forward edge ridge is opposite a rearward edge ridge at said flared rearward end, wherein said forward edge ridge and said rearward edge ridge are spaced apart by between about 13 mm and about 40 mm.

7. The tampon applicator according to claim 6, wherein said forward edge ridge and said rearward edge ridge are spaced apart by between about 17 mm and about 21 mm.

8. The tampon applicator according to claim 4, wherein a ratio of a finger grip maximum diameter to said finger grip minimum diameter is between about 1.10 to about 1.75.

9. The tampon applicator according to claim 1, wherein said finger grip section is generally concave.

10. The tampon applicator according to claim 1, wherein said at least one gripping structure includes one or more embossments, protuberances, slits, grooves; louvers, perforations, lances, abrasive medias, high wet coefficient of friction materials, pressure sensitive adhesives, or combinations thereof.

11. The tampon applicator according to claim 1, wherein said at least one gripping structure is in the shape of an arc, circle, cone, diamond, line, oval, polygon, rectangle, rib, square, triangle, or combinations thereof.

12. The tampon applicator according to claim 1, further comprising a plunger that telescopically fits into said tampon applicator through said finger grip section, said plunger having a circular cross-section, said plunger, wherein said plunger has a plunger diameter that is slightly smaller than an inner finger grip diameter, wherein said plunger diameter is between about 4 mm and about 18 mm.

13. The tampon applicator according to claim 12, wherein said plunger diameter is between about 5 mm and about 9 mm.

14. The tampon applicator according to claim 12, wherein said plunger has a rear flared end that engages said flared rearward end of said finger grip section.

15. The tampon applicator according to claim 14, wherein said rear flared end has a rear flared end diameter of between about 6 mm and about 22 mm.

16. The tampon applicator according to claim 15, wherein said rear flared end diameter is between about 12 mm and about 16 mm.

17. The tampon applicator according to claim 12, wherein said plunger has a retaining feature on a front end that engages an inner wall of said reverse taper section and/or said finger grip section, said retaining feature having a retaining feature diameter of between about 5 mm and about 20 mm.

18. The tampon applicator according to claim 17, wherein said retaining feature diameter is between about 11 mm and about 14 mm.

* * * * *